United States Patent [19]
Edison

[11] 4,040,433
[45] Aug. 9, 1977

[54] TOOTHPICK AND CONTAINER ASSEMBLY

[76] Inventor: Robert G. Edison, 3032 University Ave., Highland Park, Ill. 60035

[21] Appl. No.: 655,917

[22] Filed: Feb. 6, 1976

[51] Int. Cl.² .............................................. A61C 15/00
[52] U.S. Cl. ........................................ 132/89; 132/93
[58] Field of Search ...................... 132/89, 90, 91, 92, 132/84 B

[56] References Cited

U.S. PATENT DOCUMENTS

| 719,017 | 1/1903 | Lenhardtson | 132/89 |
| 740,586 | 10/1903 | Ohlsson | 132/89 |
| 2,481,056 | 9/1949 | White | 132/84 B |
| 2,931,370 | 4/1960 | Jackson | 132/89 |
| 2,931,371 | 4/1960 | Petitta | 132/89 |
| 3,672,378 | 6/1972 | Silverman | 132/93 |

Primary Examiner—G.E. McNeill
Attorney, Agent, or Firm—Gerald S. Geren

[57] ABSTRACT

There is disclosed herein a reusable toothpick and container assembly. The assembly includes a toothpick having an elongated blade terminating at one end in a tip for removing debris from between the user's teeth and having at the other end a cap by which the toothpick can be grasped. The container is an elongated vial, for holding mouthwash, into which the blade can be inserted and which can be sealed by the end cap. This provides for storage and cleansing of the toothpick between uses.

5 Claims, 4 Drawing Figures

U.S. Patent   Aug. 9, 1977   4,040,433
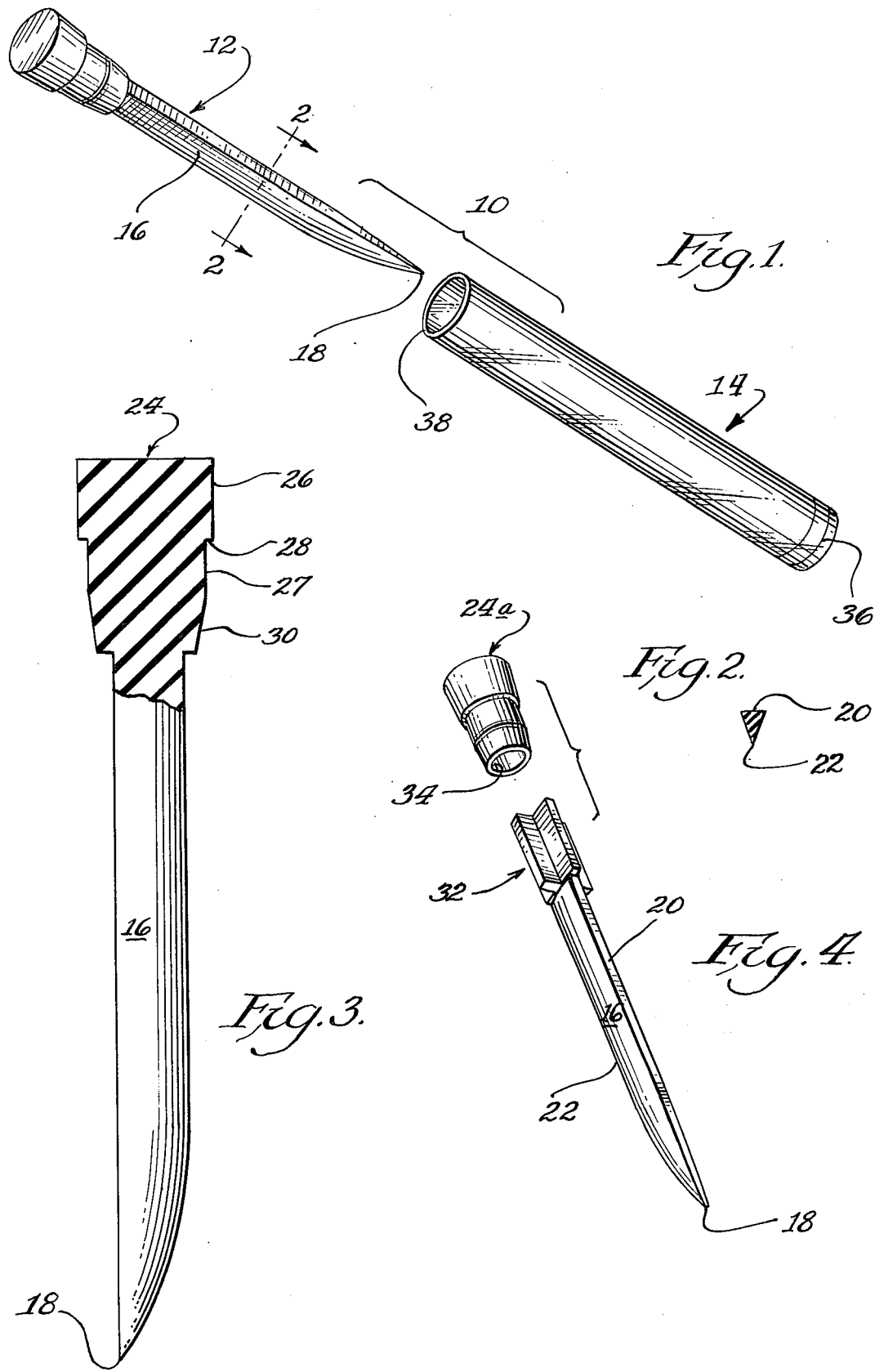

TOOTHPICK AND CONTAINER ASSEMBLY

BACKGROUND OF THE INVENTION

This invention relates to a toothpick for dislodging debris from between a person's teeth.

Wooden toothpicks for dislodging debris from between a person's teeth are well known but represents a problem in that they may splinter. Recently, a reusable plastic toothpick has been developed which is made from a relatively hard rubber and is provided with a blunt tip so as to prevent injury to the gums when the pick is being used.

Since this plastic toothpick is comparatively hard, it cannot be used to stimulate the gums.

It is therefore an object of this invention to provide a toothpick which is fabricated of a material which is sufficiently soft to permit its use as a gum stimulator.

Furthermore, existing plastic picks do not provide for storage of the toothpick between uses or for cleaning thereof. It will be appreciated that improper storage and lack of cleaning can pose a possible health hazard.

It is therefore an object of this invention to provide means for storing and cleaning a reusable toothpick between uses.

These and other objects of this invention will become apparent from the following description and appended claims.

SUMMARY OF THE INVENTION

There is provided by this invention a reusable toothpick made of a soft plastic material which is shaped to provide a blade-shaped portion that can be used to dislodge debris from between teeth and as a gum stimulator.

A tubularly-shaped, vial-like container is also provided for storing and carrying the toothpick. The container may be filled with mouthwash or other cleaning fluids for removing debris from the pick and cleansing the pick. One end of the pick can be provided with an end cap or plug which is fitted into the end of the container to seal it and render it fluid-tight. Thus the toothpick can be carried and used as needed, but kept cleansed and stored without inconvenience.

BRIEF DESCRIPTION OF THE DRAWINGS

FIG. 1 is an exploded and perspective view showing the toothpick and the vial-like container;

FIG. 2 is a cross-sectional view taken substantially along line 2—2 of FIG. 1;

FIG. 3 is a greatly enlarged elevational view of one embodiment showing an integrally-molded one-piece toothpick with a portion shown in section; and FIG. 4 is an exploded and perspective view of a two-piece toothpick.

DESCRIPTION OF THE PREFERRED EMBODIMENT

Referring now to the drawings, there is shown a toothpick and container assembly 10 generally.

The assembly includes a toothpick 12 and a vial-like container 14.

The toothpick 12 includes an elongated blade-shaped portion 16, one end of which tapers to form a tip 18. The blade-shaped portion is generally V-shaped in section and includes a flat upper surface 20, and sides which taper downwardly to form a comparatively sharp bottom edge 22. The blade-shaped portion 16 can be molded from a combination of polypropylene and polyethylene so as to provide the desired hardness and pliability for picking and softness for gum stimulation. Two different blade compositions can be provided. One can be characterized as standard for normal gums and the other soft for tender gums.

A cap or end plug 24 is provided at the end of the blade-shaped portion opposite the tip 18 for sealing the toothpick in the container 14 and for grasping by the user. In the embodiment shown in FIG. 3, the cap 24 and blade-shaped portion are integrally molded so as to provide a one-piece member. The cap is provided with an enlarged, cylindrical outer end portion 26, an outwardly tapering intermediate portion 27 which cooperates with the outer portion 26 to define an abutment shoulder 28 and an inwardly tapering end portion 30.

An alternative two-piece construction is shown in FIG. 4. In this construction, the end of the blade-shaped portion opposite the tip includes an integral cross-shaped (+) section 32 and the cap 24a includes an internal recess 34 into which the cross-shaped section is fitted. The recess and cross-shaped section are constructed so as to assure snug interfitting whereby the pick can act as a one-piece member. The external shape of the cap 24a is the same as that of the cap 24.

The vial-like container 14 is of a transparent plastic and is elongated, tubularly-shaped, has a closed bottom end 36 and an open mouth end 38. The inside diameter of the container at the mouth is slightly smaller than the outside diameter of the intermediate section so as to assure sealing engagement between the container and the cap. The stepped abutment shoulder of the cap is constructed to engage the end of the container so as to prevent the pick from being irretrievably inserted into the container. The inwardly tapered portion 30 cooperates in guiding the cap into the container. The length of the container from the mouth 38 to the end wall 36 is greater than the distance from the cap shoulder 27 to the blade tip 18 so as to prevent the tip from bottoming on the wall and preventing closure of the vial.

The container can be filled approximately one-half way with mouthwash so as to thoroughly cleanse the tip 18 and the blade-shaped portion. The container is transparent so that the user can observe the condition of the cleansing fluid and replace it as necessary.

What is claimed and desired to be secured by Letters Patent of the United States is:

1. A reusable toothpick-and-container assembly comprising: elongated, tubularly-shaped and transparent container means for holding a liquid, said container means being closed at one end and having an open mouth at the other end which is adapted to be sealed so as to provide a fluid-tight container; and molded plastic toothpick means which includes an elongated blade-shaped portion having a V-shaped cross-section and terminating at one end in a tip for picking debris from between a user's teeth, and end cap means cooperatively associated with the other end of the blade-shaped portion for grasping by the user and adapted to sealingly cooperate with said open mouth to provide said seal, said toothpick adapted to be stored within said container and in contact with a liquid therein for cleansing said toothpick for reuse.

2. A reusable toothpick-and-container assembly as in claim 1, wherein said blade-like portion and said end cap are integral.

3. A reusable toothpick-and-container assembly as in claim 1, wherein the other end of said blade-shaped portion and said cap means are separate members, each having means for cooperation in securing said cap means to said blade-shaped portion.

4. A reusable toothpick-and-container assembly as in claim 3, wherein said securement means on said blade-shaped portion includes a cross-shaped end, and said securement means on said end cap includes a recess in said cap for snugly receiving said cross-shaped end so as to secure said blade-shaped portion to said cap.

5. A reusable toothpick-and-container assembly as in claim 2, wherein said toothpick is made of polypropylene.

* * * * *